United States Patent [19]

Stock et al.

[11] Patent Number: 5,057,280
[45] Date of Patent: Oct. 15, 1991

[54] GAS MEASURING AND WARNING DEVICE

[75] Inventors: Burkhard Stock; Jürgen Krüger, both of Lübeck, Fed. Rep. of Germany

[73] Assignee: Drägerwerk Aktiengesellschaft, Lübeck, Fed. Rep. of Germany

[21] Appl. No.: 12,895

[22] Filed: Feb. 10, 1987

[30] Foreign Application Priority Data

Feb. 18, 1986 [DE] Fed. Rep. of Germany ....... 3605047

[51] Int. Cl.$^5$ ............................................. G01N 21/01
[52] U.S. Cl. .................................... 422/83; 73/61.4;
358/107; 422/59; 422/86; 422/87; 422/88;
436/164; 436/167; 436/169
[58] Field of Search ......................... 73/61.4; 358/107;
422/83, 86, 87, 88, 91, 59; 436/164, 167, 169

[56] References Cited

U.S. PATENT DOCUMENTS

| 3,074,634 | 1/1963 | Gamo | 358/107 X |
| 3,678,192 | 7/1972 | Akuta | 358/107 |
| 3,909,519 | 9/1975 | Page | 358/107 |
| 4,063,821 | 12/1977 | King et al. | 356/167 |
| 4,245,997 | 1/1981 | Wiesner | 422/91 X |

Primary Examiner—Robert J. Warden
Assistant Examiner—Timothy M. McMahon
Attorney, Agent, or Firm—McGlew & Tuttle

[57] ABSTRACT

A gas measuring and warning device includes a test tube which is traversed by the gas to be detected and with a photoelectric sampling means which contains an imaging optical system by which the test tube reaction image is projected onto the photo-sensitive row of the sensor elements. The imaging optical system contains a cylindrical lens having a cylinder axis which is parallel to the longitudinal axis of the test tube and to a row of sensor elements. Advantageously an achromatic lens as well as of an interference filter and of a pulse light source as used.

8 Claims, 1 Drawing Sheet

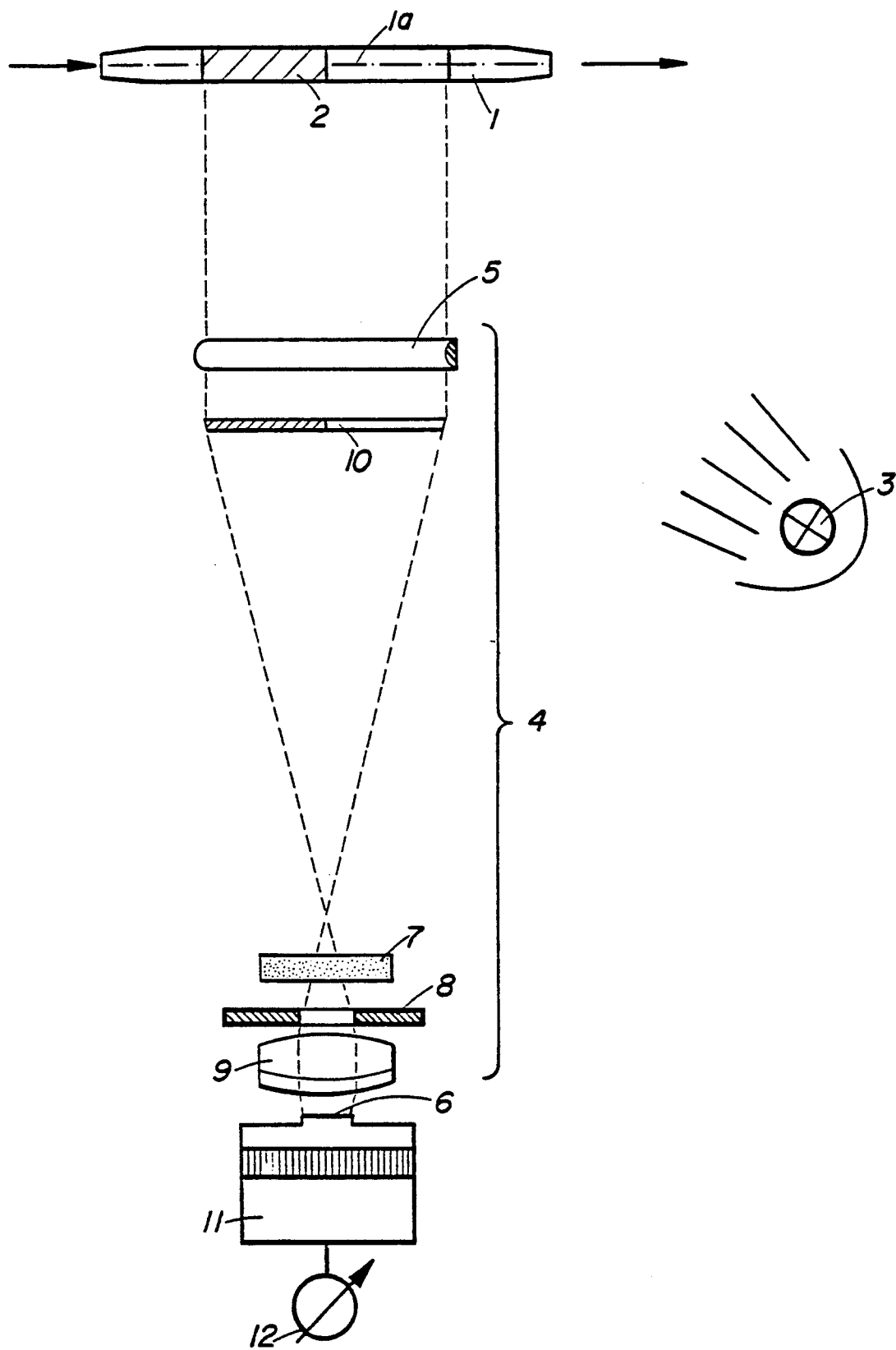

GAS MEASURING AND WARNING DEVICE

FIELD AND BACKGROUND OF THE INVENTION

This invention relates in general to gas detection devices and in particular to a new and useful gas detection measuring device into a gas measuring and warning device.

The invention relates particularly to developments of a gas measuring and warning device described in German patent application P 35 01 093.2-52, which is not a prior publication.

Such a gas measuring and warning device contains a test tube traversed by the gas to be detected as well as a photoelectric sampling means for the test tube illuminated or irradiated by at least one source of light and it comprises a photo-sensitive row of similar sensor elements for observation of a reaction zone migrating through the test tube. Connected to the photoelectric sampling means is an evaluating circuit, which is controlled by the sensor elements lying inside the reaction zone for delivery of a measurement signal. The photoelectric sampling means further contains an imaging optical system which projects the test tube onto the photosensitive row of the sensor elements for delivery of an analog output signal.

For the delivery of low noise signals from the row of the sensor elements it is necessary to design the imaging optical system so that as high as possible a light intensity occurs on the surface of the row of sensor elements, combined with a good quality of reproduction. In addition, the reproduction error of the imaging optical system is to be kept small over the entirelength of the row of sensor elements and in particular also in the edge regions. All of the measures named below thus serve to provide a photoelectric sampling means, and in particular, the imaging optical system contained therein, that a low-noise high-resolution measurement signal can be taken from the row of the sensor elements.

SUMMARY OF THE INVENTION

According to the invention, an imaging optical system contains a cylindrical lens having a cylinder axis which is parallel to the longitudinal axis of the test tube and to the row of the sensor elements. The reduced real intermediate image of the cylindrical lens is subsequently projected by an image lens, preferably an achromatic lens, onto the row of sensors. The use of an achromatic lens is appropriate because thereby the focus displacement occurring due to spherical and chromatic aberration is compensated to a large extent. With the use of an achromatic lens as an image lens, it is assured that the band of foci caused by displacement is not wider than the means distance between the two sensor elements.

A further additional improvement can be achieved in a manner known in itself, if desired, by a diaphragm place before the achromatic lens, which limits the aperture ratio for example to 2:1.

A high light intensity on the surface of the row of sensor elements can advantageously be obtained in that instead of a continuous light source a light source, is provided which is designed for delivery of light pulses. Through this pulse sampling of the light source high light intensities can be obtained briefly. Especially favorable appears to be, in consideration of the spectral composition of the radiation of the light source, the use of a gas discharge lamp.

With diode sensor rows (CCD) which may be used for the practical application there exists a maximum sensitivity in the range of visible light approximately between 600 and 900 nm. A correspondingly adapted gas discharge lamp should thus have a high light component in this range.

Depending on the type of the gases to be detected in the test tube, it may be necessary to provide an additional explosion protection for the gas discharge lamp.

Lastly, in the sense of the problem posed, the quality of reproduction can be further improved in that an interference filter is inserted between the cylindrical lens and the achromatic lens. Thereby an increase in contrast between the parts with gas and without gas in the test tubes can be obtained.

Accordingly it is an object of the invention to provide a gas measuring device for measuring an indicated reaction image produced by the passage of a gas over an indicating material which comprises a test tube which has a reaction imaging area which reacts to the passage of the gas therethrough to produce a reaction image and including an imaging optical system which includes a cylindrical lens having a cylindrical axis arranged parallel to and spaced from the test tube and an image evaluating system including a row of sensors and means for projecting the reaction image through the cylindrical lens onto the row of sensors.

A further object of the invention is to provide a gas measuring and a warning device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE of the drawings is a schematic representation of a gas measuring and warning device constructed in accordance with the invention.

DESCRIPTION OF THE PREFERRED EMBODIMENT

Referring to the drawing in particular, the invention embodied therein comprises a gas measuring device for measuring an indicated reaction image 2 which is formed by the passage of a gas over an indicating material arranged within a test tube 1 in which gas enters through one end of the test tube and exits from the opposite end. In accordance with the invention, a cylindrical lens 5 is arranged so that the axis of its cylinder is parallel to the axis 1a of the test tube 1. An imaging evaluating system 11 includes a row of sensors 6 and the apparatus includes means for projecting reaction image 2 onto the row of sensors which includes the cylindrical lens 5 and the imaging optical system 4 and the illuminating lamp 3.

Present in the test tube 1 is a reaction zone 2 which is a coloring or imaging reaction. The test tube 1 is illuminated by a laterally disposed gas discharge lamp 3.

An imaging optical system 4 contains a cylindrical lens 5, the cylinder axis of which is disposed parallel to the longitudinal axis 1a of the test tube 1 and to a diode row of sensor elements 6. In the imaging optical system 4 are provided further an interference filter 7, a diaphragm 8, and an achromatic lens 9. The gas discharge lamp 3, the imaging optical system 4 and the diode row 6 together form the photoelectric sampling means.

The cylindrical lens 5 produces a reduced real intermediate image of the test tube 1 or of the reaction zone thereof, which image is indicated at an engaging position 10. This real intermediate image is projected, with interposition of the interference filter 7 and diaphragm 8, through the achromatic lens 9 onto the length of the diode row 6.

The output signals of the diode row 6 are supplied to an evaluating circuit 11 schematically shown in the drawing, which via a built-in shift register permits readout of the diode row with a timing preset accordingly. The evaluating circuit contains a preamplifier as well as an analog/digital converter for digital conversion of the signals read out of the diode row 6, as well as a first digital memory in which these signals, recorded before a possible gasification, are stored. The evaluation circuit further contains a second digital memory, which stores the likewise binary converted sample values after gasification. In addition, a digital arithmeticunit for signal processing in the form of a microcomputer is provided, which delivers output values for measurement display unit 12 or respectively for actuating a warning signal.

While specific embodiments of the invention have been shown and described in detail to illustrate the application of the principles of the invention, it will be understood that the invention may be embodied otherwise without departing from such principles.

What is claimed is:

1. In a gas measuring and warning device including a test tube having a reaction substance forming a reaction image when it is traversed by a gas to be detected, photoelectric sampling means for the test tube and an evaluating circuit connected to said photoelectric sampling means for producing a measurement signal; the improvement wherein said photoelectric sampling means comprises, in combination: at least one source of light directed at the test tube reaction image, a row of photosensitive sensor elements for observation of said reaction image, and an imaging optical system including a cylindrical lens having a cylinder axis which is parallel to the longitudinal axis of said test tube and to said row of photosensitive sensor elements and an imaging lens for projecting an intermediate test tube reaction image produced by said cylindrical lens onto said row of photosensitive sensor elements.

2. A gas measuring and warning device according to claim 1, wherein said imaging optical system contains an achromatic imaging lens.

3. A gas measuring and warning device according to claim 1, wherein said imaging optical system contains an interference filter.

4. A gas measuring and warning device according to claim 1, wherein said light source includes means for delivering light pulses.

5. A gas measuring and warning device according to claim 1, wherein said light source comprises a gas discharge lamp.

6. A gas measuring device for measuring an indicated reaction image produced by the passage of a gas over an indicating material comprising a test tube having a reaction image area which reacts to the passage, of a gas through the test tube to produce a reaction image, a source of light directed at the test tube reaction image area, an imaging optical system arranged adjacent to said test tube including a cylindrical lens having a cylinder axis raised parallel to and spaced from said test tube, an image evaluating system including a row of photosensitive sensors, and means for projecting a reaction image through said cylindrical lens onto said row of photosensitive sensors.

7. A gas measuring device according to claim 6, wherein said imaging optical system includes a filter, a diaphragm and an achromatic lens disposed between said cylindrical lens and said row of photosensitive sensors.

8. A gas measuring device for measuring an indicated reaction image produced by the passage of a gas over an indicating material, comprising a test tube having a reaction image area which reacts to the passage of a gas through the test tube to produce a reaction image, means for directing pulses of light at said test tube, an image evaluating system including a row of photosensitive sensors, and an imaging optical system arranged adjacent to said test tube including a cylindrical lens having a cylinder axis which is parallel to and spaced from said test tube, an achromatic imaging lens disposed between said cylindrical lens and said row of photosensitive sensors, an interference filter disposed between said cylindrical lens and said imaging lens and a diaphragm disposed between said interference filter and said imaging lens.

* * * * *